United States Patent
Wiesmann et al.

(10) Patent No.: US 7,181,264 B2
(45) Date of Patent: Feb. 20, 2007

(54) METHOD AND APPARATUS FOR NONINVASIVE PHYSIOLOGIC MONITORING

(75) Inventors: William P. Wiesmann, Washington, DC (US); Loland A. Pranger, Gaithersburg, MD (US); Mary S. Bogucki, Branford, CT (US)

(73) Assignee: Sekos, Inc., Germantown, MD (US)

( * ) Notice: Subject to any disclaimer, the term of this patent is extended or adjusted under 35 U.S.C. 154(b) by 366 days.

(21) Appl. No.: 10/387,138

(22) Filed: Mar. 12, 2003

(65) Prior Publication Data

US 2003/0212315 A1   Nov. 13, 2003

Related U.S. Application Data

(60) Provisional application No. 60/363,600, filed on Mar. 12, 2002.

(51) Int. Cl.
*A61B 6/00* (2006.01)

(52) U.S. Cl. ............... 600/473; 340/573; 128/201; 455/100; 455/66

(58) Field of Classification Search ............ 600/472, 600/476, 473, 322, 474, 323; 128/204.23, 128/201; 340/573; 455/100, 66
See application file for complete search history.

(56) References Cited

U.S. PATENT DOCUMENTS

| | | | | |
|---|---|---|---|---|
| 4,510,938 A * | 4/1985 | Jobsis et al. | ............ | 600/344 |
| 4,802,485 A * | 2/1989 | Bowers et al. | ............ | 600/324 |
| 5,584,296 A * | 12/1996 | Cui et al. | ............ | 600/479 |
| 5,779,631 A * | 7/1998 | Chance | ............ | 600/328 |
| 5,902,235 A * | 5/1999 | Lewis et al. | ............ | 600/323 |
| 5,990,793 A * | 11/1999 | Bieback | ............ | 340/573.1 |
| 6,681,128 B2 * | 1/2004 | Steuer et al. | ............ | 600/322 |
| 6,805,673 B2 * | 10/2004 | Dekker | ............ | 600/529 |
| 2003/0144699 A1 * | 7/2003 | Freeman | ............ | 607/5 |
| 2005/0059869 A1 * | 3/2005 | Scharf et al. | ............ | 600/340 |

OTHER PUBLICATIONS

Jubran, A., Principles and Practice of Intensive Care Monitoring, NY/McGraw-Hill 1998, pp. 261-287.*

* cited by examiner

Primary Examiner—Brian L. Casler
Assistant Examiner—Joel M. Lamprecht
(74) Attorney, Agent, or Firm—Abanti Bhattacharyya, esq.; Bartunek & Bhattacharyya, Ltd.

(57) ABSTRACT

Intense environmental or working conditions can impede an individual's evaporative cooling mechanism normally responsible for thermoregulation during exercise or exertion. Non-invasive physiological monitoring capabilities are needed to more precisely define the cardiovascular responses and identify markers of impending failure of compensatory mechanisms prior to collapse or onset of irreversible pathology. The oximetry method and system of the present invention provides non-invasive, continuous remote monitoring and analysis of cardiovascular and pulmonary function that overcomes accuracy and monitoring deficiencies of current oximetry systems.

2 Claims, 2 Drawing Sheets

METHOD AND APPARATUS FOR NONINVASIVE PHYSIOLOGIC MONITORING

This application claims priority from U.S. Provisional Application 60/363,600 filed Mar. 12, 2002.

GOVERNMENTAL INTEREST

The invention described herein may be licensed by or for the United States Government under 37 CFR 401.14, wherein the United States Government shall have a nonexclusive, nontransferable, irrevocable, paid-up license to practice or have practiced for or on behalf of the United States the subject invention throughout the world.

BACKGROUND OF THE INVENTION

The human body's thermoregulation system can be stressed by many conditions. Athletes, workers operating in confined/restricted spaces or firefighters are subject to extreme environmental conditions, protective clothing and heavy equipment that can impede their evaporative cooling mechanisms, and exert physiological stresses on their systems.

A human's thermoregulation system normally adjusts to meet physiological stresses that occur with exertion. At the onset of exercise, healthy adults experience a rapid increase in cardiac output. Stroke volume also increases with augmentation of venous return from the periphery and resulting inotropic enhancement based on Frank-Starling forces governing myocardial contractility. As exercise progresses, blood volume is redistributed to the working muscles to meet oxygen demands, and to the skin for dissipation of the heat being produced by the muscles. Ongoing exercise decreases stroke volume due to vascular redistribution of blood volume together with volume loss due to sweating. Cardiac output is maintained by compensatory increase in heart rate to an individual maximum dependant upon the individual's age and conditioning. Respiration rates also increase during exercise. The combination of increased respiratory rates, evaporative sweat loss and redistribution of blood to capillary beds in the skin provide adequate cooling to maintain body temperatures within acceptable parameters.

This thermoregulatory process can be impeded when a person is involved in heavy exertion with dynamic/aerobic and static/anaerobic components. Firefighters' activities, for example, require carrying heavy equipment while wearing thermal and flame resistant protective ensembles (including self-contained breathing apparatus, SCBA) that quantitatively prevent evaporative loss of metabolic heat. This is due to the nature of their protective gear and the work environment (in temperatures in range of 700 degrees F. and upwards), which collectively prevent heat dissipation to the environment. Under these conditions, the cardio-accelerator compensation that normally maintains cardiac output during exercise is lost resulting in an almost immediate reduction in cardiac output with initiation of exertion and sweating. Decreased cardiac output leads to a constriction of the peripheral vasculature to maintain systolic blood pressure, which in turn leads to a rapid rise in core temperature that remains even after exercise ceases. The effect is that of a cascade of sequential failure of compensatory mechanisms.

Remote, non-invasive medical monitoring would greatly reduce the chance of impending failure if it was capable of identifying physiological parameters that indicate the achievement of near-maximal work capacity prior to cardiovascular collapse, symptomatic heat illness or other adverse clinical outcomes. However, this type of monitoring, in real time, offers significant technical challenges.

The sensor system must support rapid data collection, processing and effective transmission over sufficient distances to monitor the person(s) operating in the particular environment. These sensors must input/access individual biological signals, under time constraints, or must perform in severe environments without adding excessive weight to the wearer or impede dexterity or mobility of the wearer.

U.S. Pat. No. 6,199,550 to Wiesmann, et al., incorporated herein by reference, discloses and claims a self contained breathing apparatus (SCBA)-based sensor system that is positioned on an interior portion of a respiratory mask to allow transmission of physiological parameters to a remote location. Particularly, this patent discloses a pulse oximeter system that utilizes light at two wavelengths to be passed through a pulsatile tissue bed in a manner that then allows the light to be modulated by the pulsatile component of arterial blood. Continuous adjustment of the incident light provides for individual variations such as skin color, flesh thickness, etc. Through mathematical iterations, this pulsatile signal provides information on the pulse rate, oxygen saturation, and blood perfusion of the individual being monitored.

Pulse oximetry is a well-established, non-invasive medical sensor that detects alterations in hemoglobin oxygen saturation and measures arterial oxygen saturation based on spectrophotometric principles. The hardware utilized by these sensors have proved rugged enough to support application in extreme environments and be utilized into the SCBA face mask, as taught in U.S. Pat. No. 6,199,550B1 to Wiesmann, et al.

Pulse oximetry is particularly useful because of the nature and amount of physiologic information that can be derived from it. Vital signs such as heart rate, blood pressure and arterial oxygen saturation are relatively late indicators of compromised tissue perfusion in patients being monitored for severe medical or surgical conditions. Increased heart rate is a nonspecific sign that is associated with fever, emotional state, endocrine abnormalities and several other factors. When used as an indicator of volume depletion, tachycardia is relatively insensitive, requiring loss of 15–25% of total intravascular volume. This translates to 7–10 liters of fluid from a 70 kg adult. Loss of blood pressure is even less sensitive, and arterial oxygen saturation is maintained until full cardiovascular collapse occurs. Pulse oximetry would therefore appear to have minimal value in detecting sub-clinical fluid depletion or cardiovascular inadequacy for work demands in an arena involving individuals subject to extreme environments or hazardous work conditions.

In the critical care setting, subtle alterations in tissue perfusion are inferred by monitoring indirect indicators such as lactic acid production, biochemical markers of end organ injury and oxygen saturation in mixed venous blood. Mixed venous blood requires cannulation of the pulmonary artery and performance of co-oximetry on intermittently obtained blood samples. Current oximetry technology again appears not to be amenable to real-time monitoring.

Studies suggest that the earliest metabolic changes of hypoperfusion are detectable by measurement changes in the DC signal. Transcutaneous oxygen and carbon dioxide monitors were recently used as part of a non-invasive suite that also included pulse oximetry and estimation of cardiac output by thoracic bioimpedance. Data from this suite was found to correlate well with hemodynamic measurements by conventional, invasive devices in ICU patients. Analysis of the plethysmographic waveform generated by pulse oximeters was also found to correlate with volume status in mechanically ventilated patients under general anesthesia. These findings suggest that both the AC and DC components should be monitored (as opposed to only the AC) for accurate results.

Current pulse oximeters measure light absorption through living tissue via an alternating current (AC) or pulsatile component and a direct current (DC) component. The AC component is the pulsatile expansion of the arteriolar bed with arterial blood, while the DC component represents the absorbencies of the tissue beds such as venous blood, capillary blood and nonpulsatile arterial blood, as shown in FIG. 1. See Jubran, A., *"Principles and Practice of Intensive Care Monitoring,"* 1998, p. 261–287.

Based on the assumption that arterial blood provides the only pulsatile absorbance between the light source and its photodetector, current pulse oximeters utilize light-emitting diodes in the red and infrared regions. These wavelengths allow oxyhemoglobin and hemoglobin to absorb light at different rates. Specifically, hemoglobin absorbs greater light in the red region, whereas oxyhemoglobin absorbs greater light in the infrared region. The diodes are rapidly switched on and off and the pulse oximeter then measures the AC or pulsatile component of light absorbance at each wavelength and then divides this by the corresponding DC component to obtain a computation that is independent of ambient light intensity, and that can be utilized to calibrate against direct arterial blood measurements. Utilizing the pulsatile signals and other computational schemes pulse oximeters also measure pulse rates. See Jubran, id.

While effective, current pulse oximeters have inherent drawbacks and suffer from uniform accuracy, particularly when fractional oxygen saturation is 80% or less. Studies on non-critically ill and critically ill patients showed that current pulse oximeters did not provide accurate readings when fractional oxygen saturation was at 63%. See Jubran, id.

State-of-the-art pulse oximeters provide sufficient accuracy medical monitoring of potentially hypoxemic conditions in resting individuals in controlled environments. However, they do not provide satisfactory monitoring for early signs of physiologic stress under extreme conditions as needed by firefighters and others working or operating under extreme conditions. Therefore, there is a need to provide a manner of noninvasive physiological monitoring that overcomes the drawbacks of the prior art.

No system or methodology that uses pulse oximetry can provide such measurements, as current pulse oximeters only evaluate pulsatile signals (while using the DC signal for mathematical calculations only). This correlates with oxygen saturation of arterial blood, which is maintained by physiologic compensatory mechanisms until cardiovascular collapse intervenes. This occurs too late to be valuable in monitoring firefighters, as this is the condition that is to be prevented, not simply observed.

The present invention, therefore, overcomes the drawbacks of current pulse oximeters by providing a methodology and system that is capable of measuring DC components as well as the AC components, for optimal monitoring and accuracy in extreme conditions, as described herein below.

SUMMARY

It is, therefore, an objective of the present invention to provide a method and system for unencumbered monitoring of heart rate and oxygen saturation of both pulsatile (AC components) and non-pulsatile (DC components) tissue compartments.

It is yet another objective of the present invention to provide a method and system for unencumbered monitoring of heart rate and oxygen saturation utilizing a face-piece mounted sensors, SCBA mounted sensors, radiotelemetry and processing software.

These and other objectives are realized by the present invention.

DETAILED DESCRIPTION OF THE PREFERRED EMBODIMENTS

Figure 1:
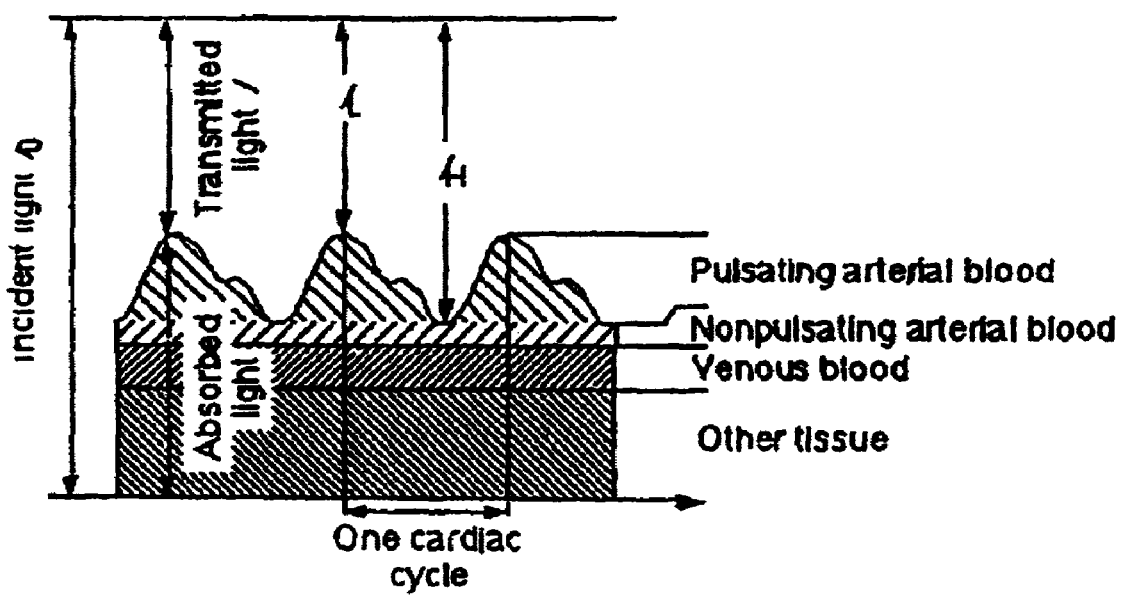
FIG. 1 is a schematic of the AC and DC components as determined utilizing prior art oximetry technology.

The present invention is directed to pulse oximetry technology that overcomes the drawbacks of current pulse oximeters and provides a method of obtaining several physiological parameters previously undeterminable without invasive procedures. Specifically, the present invention provides a novel and useful method of utilizing previously unused DC signals to obtain non-pulsatile readings. These non-pulsatile readings are further analyzed to obtain accurate physiologic parameters which were previously unattainable through AC/pulsatile components or non-invasive methodology.

This novel methodology is based on absorbance of red and/or infrared light by non-pulsatile (DC) components including skin pigmentation, bone, other tissues, nonpulsating arterial blood and venous blood. The non-pulsatile components can be separated into categories, including those that remain constant over time and those that will change over time (durational, ignoring the pulsatile component). Constant parameters include skin pigmentation and or bone, restrictive tensions on vascular beds dependant upon tension or the tension caused by the placement of the sensor. Variable parameters include oxygenation saturation of hemoglobin in other tissue beds, nonpulsating arterial blood and venous blood.

The methodology of the present invention provides a DC component, or rather changes in the DC component over time, correlating to mixed venous oxygen saturation, cardiac output, tissue perfusion and tissue oxygen demand. These physiologic parameters can now be obtained non-invasively and enhances physiologic monitoring.

It is important to note that even when the AC component is subject to motion artifact, the DC component remains unaffected and insulated from the motion. This feature provides the added benefit of maintaining a robust DC signal in extreme conditions or environments.

Test Results:

Utilizing a Spirotroniq® S model SCBA face masks, reflectance mode pulse oximetry sensors were added to the reflected rubber lining of the face piece that forms the seal with the wearer's forehead. The oximetry sensors were mounted to the opposite side of the lining. The space between the forehead reflection and the clear shield attachment to the face piece provides a channel to accommodate the bulk of the LED emitter and detector components as well as the wiring. The wiring exists near the attachment of the low-pressure air line so that it can be easily added to existing wiring and operate with the low pressure line back to the electronics box attached to the base of the SCBA harness.

Previous testing had indicated that the forehead is a suitable location for placing pulse oximetry sensors. The airtight seal required by the National Institute for Occupational Safety and Health requires continuous contact with the integrated sensors. The series of head straps designed to secure the seal with the face reduces the incidence of motion artifact, a common problem with ambulatory pulse oximetry. Some variability had been noted among different wearers in reliability of signal acquisition during previous work with SCBA-mounted oximeters. This was suspected to be due to the placement of the emitting and detecting components of the oximetry sensors in the face pieces.

Figure 2:
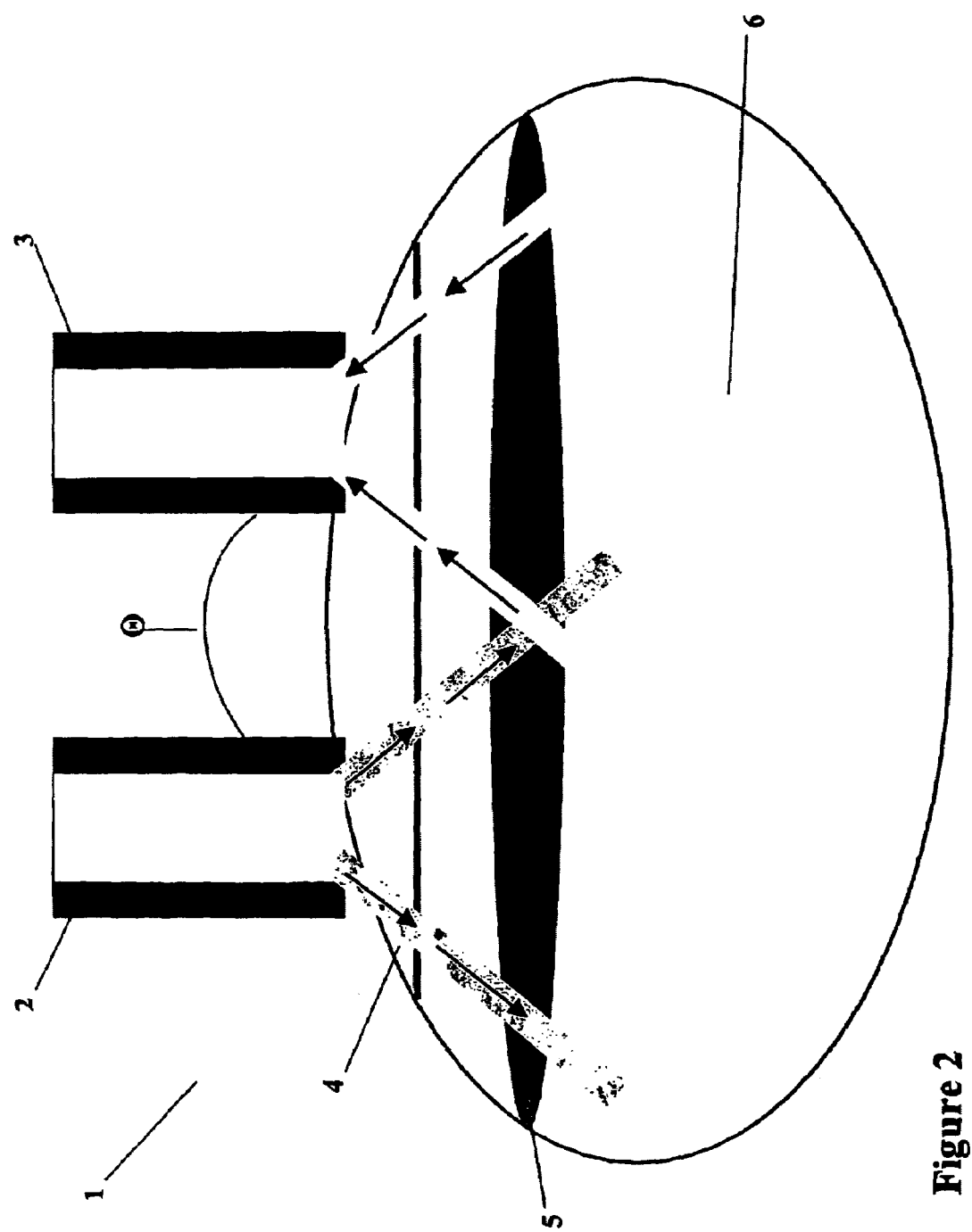
FIG. 2 is a schematic of a SCBA mask having a pulse oximeter and the method of using in accordance to the present invention.

The SCBA mask(s) 1 as disclosed and taught by Wiesmann et al, discussed above, were modified for use with the present invention. As shown in FIG. 2, the optimal distance between the LED emitters 2 and detectors 3 at the particular angle θ imposed by the contour of the mask 1 fitting the forehead was determined using volunteer subjects with differing face shapes and skin characteristics. The mask was placed on the individual's face such that the emitters 2 and detectors 3 were flush with the mask 1 and perpendicular to the individual's forehead.

In use, a light array supplied by the emitters 2 enters the forehead 4, the capillary bed 5 and bounces off bone 6. This light is then detected by the detector 3. The detected light signal is then sent to a remote processor (not shown) to obtain physiologic parameters.

An SCBA mask was fitted with a 9-pin sub-miniature D connector that is commonly used by oximeter manufacturers. Because most oximeter manufactures utilize charts and tables to translate the infrared to red signal ratio into oxygen saturation ($SpO_2$) levels, it is important to note that the accuracy of the calculated $SpO_2$ value is dependent upon re-calibration when using sensors and processors from different manufactures.

The oximetry system performs a direct calculation of the plethysmographic data through a processor board. The data are stored on a memory card attached to the processor system, while a small sub-set of the data is telemetered to a remote CPU using a wireless serial connection. This small sub-set of data is utilized as a quality check.

What is claimed is:

1. A method of using a SCBA mask having emitter and detector sensors for obtaining non-invasive pulsatile physiologic parameters and non-pulsatile physiological parameters comprising the steps of:
   (a) determining optimal distance between said emitters and said detectors;
   (b) placing and securing said mask on an individual's face and reducing incidences of motion artifact and orienting said emitter and detector sensors perpendicular to said individual's forehead;
   (c) supplying a light array from said emitter to said individual's forehead and capillary bed and bounding said array off said individual's bone'
   (d) detecting and transmitting said light to a remote processor;
   (e) obtaining said physiologic parameters pertaining to said pulsatile parameters and said non-pulsatile parameters;
   (f) correlating said physiologic parameters to optimal monitoring and accuracy of individuals using said SCBA mask in extreme conditions;
   (g) using direct current signals and obtaining constant and variable non-pulsatile readings;
   (h) analyzing said non-pulsatile readings and obtaining said non-pulsatile physiologic parameters;
   (i) using alternating current signals and obtaining pulsatile readings; and
   (j) analyzing said pulsatile readings and obtaining said pulsatile physiologic parameters.

2. A method for obtaining physiological parameters as recited in claim 1, wherein said non-pulsatile physiological parameters comprise mixed venous oxygen saturation, cardiac output, tissue perfusion and tissue oxygen demand, and wherein said constant non-pulsatile readings comprise skin pigmentation, restrictive tensions on vascular beds and tensions caused by sensor placement; and wherein said variable non-pulsatile readings comprise oxygenation saturation of hemoglobin in tissue beds, non-pulsating arterial blood and venous blood.

* * * * *